US006896579B2

(12) United States Patent
Bromenshenk et al.

(10) Patent No.: US 6,896,579 B2
(45) Date of Patent: May 24, 2005

(54) METHOD AND APPARATUS FOR CONDITIONING HONEY BEES

(75) Inventors: Jerry Bromenshenk, Missoula, MT (US); Robert A. Seccomb, Missoula, MT (US); Steven D. Rice, Victor, MT (US); Robert T. Etter, Missoula, MT (US); Colin B. Henderson, Missoula, MT (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 10/631,176

(22) Filed: Jul. 30, 2003

(65) Prior Publication Data

US 2004/0077289 A1 Apr. 22, 2004

Related U.S. Application Data

(60) Provisional application No. 60/399,616, filed on Jul. 30, 2002, and provisional application No. 60/400,034, filed on Jul. 30, 2002.

(51) Int. Cl.$^7$ .............................................. A01K 53/00
(52) U.S. Cl. ............................................ 449/2; 449/48
(58) Field of Search ............................ 449/1, 2, 9, 10, 449/11, 48; 119/6.5, 61, 72, 77

(56) References Cited

U.S. PATENT DOCUMENTS 2,492,468 A * 12/1949 Durben .......................... 449/9
4,322,862 A * 4/1982 Beuthling ..................... 449/48

(Continued)

FOREIGN PATENT DOCUMENTS

WO   WO 01/77283   10/2001

OTHER PUBLICATIONS

Bromenshenk, J; Can honey bees be trained to find land-mines?; Biosciences Info. Service, Biosis [Online], Feb. 17, 2000, Database access. #XP002267259; Philadelphia, PA, US and.

Highfield, R; Honey bees recruited to pinpoint land–mines; Internet Article [Online]; Apr. 29, 1999; Database access. #XP002267260; abstract.

Bromenshenk, J; Can honey bees assist in area reduction and landmine detection?; Internet Article [Online] pp. 1–6; Database access. #XP002267261, The Univ. of MT, MT, US.

Anonymous; Active monitoring, conditioning of bees to find chemicals and devices; Internet Article [Online]; Database access. XP00267262, The Univ. of MT, MT, US; abstract.

Primary Examiner—Robert P. Swiatek
(74) Attorney, Agent, or Firm—Saliwanchik, Lloyd & Saliwanchik

(57) ABSTRACT

A method to condition honey bees to search for a non-rewarding producing target odor source enables bees to identify a number of chemical substances such as those associated with unexploded ordnances, land mines, and illicit drug laboratories. Further, the subject method can be used to increase pollination efficiency by conditioning the bees to search for a specific vapor from a target crop. The method includes conditioning the bees to the target odor by moving their hives into a staging area. The staging area is located at least two miles from the ultimate site to be searched. The target odor is applied to the hive. Bulk feeders containing the target odor are placed near the hive. The hives are reoriented to the bulk feeders for several days. The hives are then moved to the search site and feeding/conditioning trays containing the target odor are placed nearby. For the first, approximately 24 hours, the bees are fed from the feeding/conditioning trays. Thereafter, periods of feeding and starvation are alternated to encourage the bees to forage and identify the target source. There are several embodiments of the feeding/conditioning trays which present the target odor to the bee during conditioning. Additionally, an automated feeding controller is useful in the conditioning method.

23 Claims, 4 Drawing Sheets

U.S. PATENT DOCUMENTS

| | | | | |
|---|---|---|---|---|
| D326,742 S | * | 6/1992 | Tart | D30/130 |
| 5,277,647 A | * | 1/1994 | Earl | 449/2 |
| 5,377,617 A | * | 1/1995 | Harwich | 119/6.5 |
| 5,647,299 A | * | 7/1997 | Pearson-Falcon | 119/61 |
| 6,595,828 B2 | * | 7/2003 | Page et al. | 449/2 |

* cited by examiner

METHOD AND APPARATUS FOR CONDITIONING HONEY BEES

CROSS-REFERENCE TO RELATED APPLICATIONS

This application claims the benefits of U.S. Provisional Patent Application Nos. 60/399,616, filed Jul. 30, 2002 and 60/400,034, filed Jul. 30, 2002. The disclosures of each of these applications are hereby incorporated by reference in their entirety, including all figures, tables, and drawings.

The subject invention was made with government support under a research project supported by the Defense Advanced Research Projects Agency (DARPA), Grant No. N66001-98-8630, Amendment #P0005. The government has certain rights in this invention.

BACKGROUND OF THE INVENTION

Nearly 2/3 of the food crops used by humans depend on effective pollination by honey bees for optimum yields. Onions take two years to make a seed crop. There are times when the bees work an onion field very well, and others when they decide not to work at all. Onions are grown in more than 20 states. Domestic onion production in the U.S. alone consists of approximately 145,000 acres of onions, which produce about 6 billion pounds of onions each year. The U.S. industry accounts for 2.5 percent of the world onion acreage and 7 percent of the world production. The annual value of the U.S. crop is $800 million at the farmgate and nearly $3–4 billion at retail. In order, however, to achieve constancy of maximum production of the onions there must be pollination by the bees.

Pollination relies entirely on bees' self selection, and thus requires overstocking of bees for extended time periods. There is always a risk that in areas with a high abundance of other food sources, honey bees will not be effective pollinators, because of a tendency to exploit these other sources. Conditioning honey bees to search for specific vapors however would allow for selective pollination. The specific vapors for which the honey bees are conditioned to search need not be components of the natural environment. For example, explosives and compounds associated with illicit drug manufacture emit novel chemical vapors. These vapors are not components of the natural environment. Honey bees could be conditioned to identify unexploded ordinances (UXOs) and assist in clearing land mines. Using current technologies, finding the origin of novel chemical vapor sources like unexploded ordinances (UXOs) and buried land mines is difficult and time consuming. For example, in Croatia, clearing suspected mined area has the highest priority. There are more than 1,700 sq km that remain to be cleared in Croatia. Current clearing and demining occurs at an annual capacity of 50 sq km. Finding illicit drug manufacturing laboratories which also emit novel chemical odors is likewise difficult and time consuming. Since these vapors are not natural, there is no chance that bees can be used to detect and localize such compounds without conditioning.

Currently, there are no behavioral modification programs or equipment for conditioning honey bees to actively search for a single, non-reward producing source. Since standard methods for honey bee pollination generally rely entirely on chance and nature to accomplish pollination, the use of chemical attractants or repellents has proven to be unpredictable, with variable success.

All patents, patent applications, provisional patent applications and publications referred to or cited herein, are incorporated by reference in their entirety to the extent they are not inconsistent with the explicit teachings of the specification.

SUMMARY OF THE INVENTION

The subject invention is a method of conditioning honey bees to focus the bees' foraging on a single chemical odor signature. The signature can be a pure compound or a mixture that presents a distinct odor detectable by bees. The subject method enables bees to be conditioned on a variety of chemicals important to the military, law enforcement, and homeland defense as well the chemical signatures from a wide variety of important but difficult to pollinate crops. This unique behavioral modification program allows bees to be kept searching for more than 30 days without shifting to alternate sources.

The subject method involves conditioning bees in their hives by moving the hives to a staging area at least two miles from a designated search area. The target odor is applied to the hives. Additionally, bulk feeders containing the target odor are placed near the hives. Over the course of the next 24 to 48 hours the bulk feeders are repositioned several times within the staging area and the bees are reoriented to the food and odor source. The hives are then moved to the search area. In the search area, feeding/conditioning means are placed about two meters from each hive. The feeding/conditioning means contain the target odor. The bees are fed for the first 24 hours in the search area. Then periods of feeding and starvation are alternated to encourage the bees to forage, search for and identify the target odor. Conditioning bees by the subject method enables bees to be kept searching for more than 30 days without shifting to an alternate source of food.

The method of the subject invention utilizes unique feeder/conditioning means. One embodiment of the feeding/conditioning means is in the form of a feeding plate. The feeding plate sits low to the ground to encourage the bees to forage at ground level. The plate has a central feeding well encircled by a channel in which the target odor is placed. Screen is placed over the feeding well and channel allowing the bees to light and feed while being exposed to the target odor. Another embodiment of the subject feeding/conditioning means is in the form of a feeding trough and is useful for conditioning larger numbers of bees. The trough likewise exposes the bees to the target odor when they are feeding. Both the trough and the plate have overfill prevention means that can be incorporated into automated feeding controller delivery means to assist in alternating periods of feeding and starvation of the conditioned bees.

DETAILED DESCRIPTION OF THE INVENTION

Figure 1:
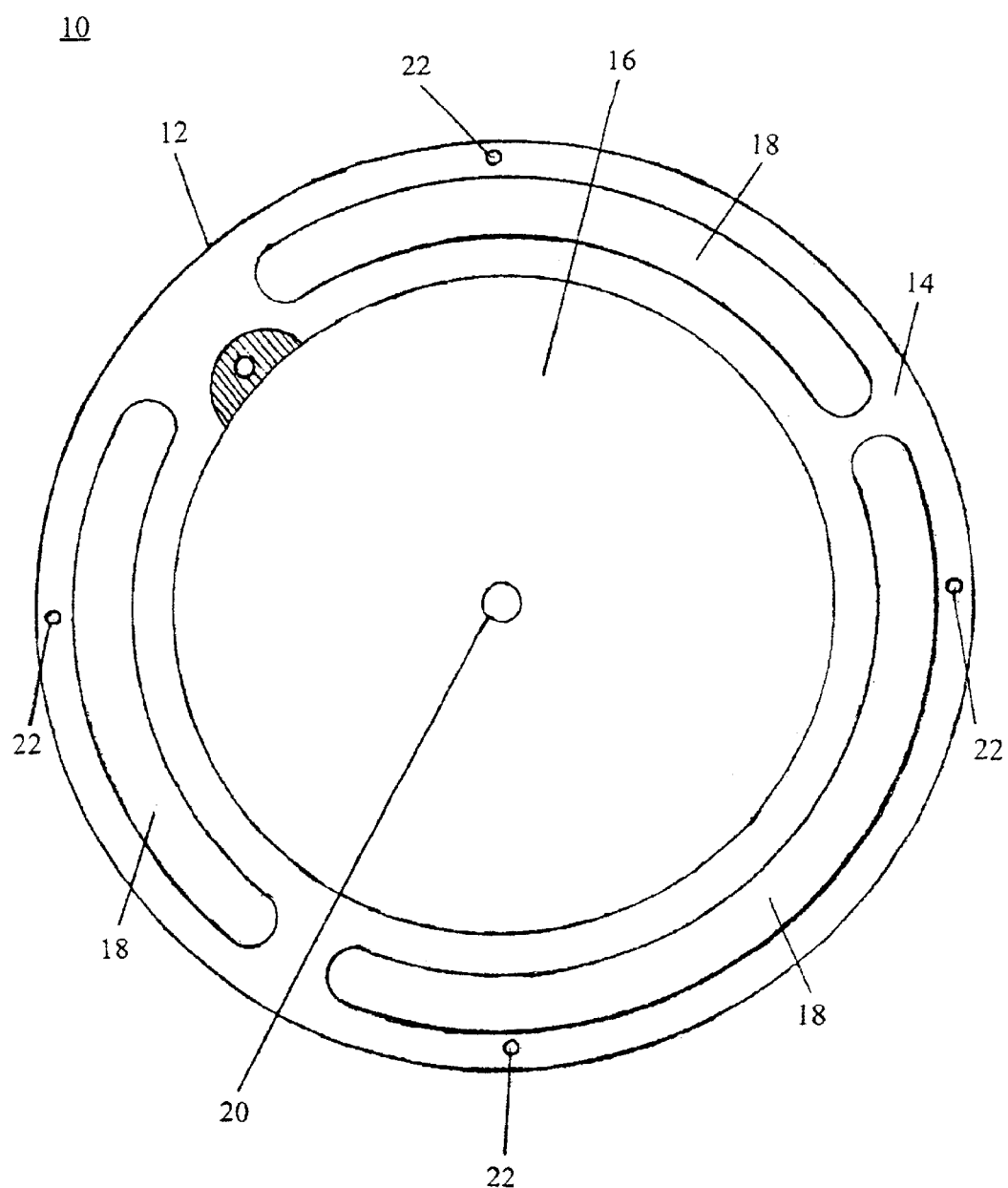
FIG. 1 is a top plan view of a preferred embodiment of the feeding/conditioning means of the subject invention.

The subject invention involves a method of conditioning bees to search for a specific odor. The bees are conditioned to seek out a non-rewarding source and will continue to seek that source for more than 30 days. Devices to facilitate these methods including feeding/conditioning means and a controller delivery feeding system are also described.

The method used to condition honey bees to search for specific chemical signatures in the environment utilizes their natural behaviors. It is necessary to break any focus the bees may have on existing natural food resources and entrain them on an artificial food substrate that is marked with the new chemical odor for which the bees are to be directed to search. Generally, the process is initiated by pre-positioning bee hives in a staging area at least 2 miles from the designated search area, applying the target odor to the hives, placing bulk feeders marked with the target odor near the hives, repositioning the bulk feeders about the hives for about 24 to 48 hours, moving the hives to the search area, placing feeding/conditioning means near the hives, feeding the bees from the feeding/conditioning means for 24 hours and thereafter alternating periods of feeding and starvation to encourage the bees to forage and identify the target odor.

Specifically, beehives are placed in a staging area where the bees are introduced to the target odor. The staging area is at least two miles from the search area to prevent foraging bees from entering the search area before they are conditioned to the target scent. The target odor is introduced to the bees by incorporating the odor into their hives as well as their food source. In a preferred embodiment, scent packets are suspended between frames within each hive. Scent packets are prepared by wrapping about 1 to 4 grams of the target odor source in porous filter paper. The filter paper packets are then wrapped in aluminum window screening. Saturating the hive with the target odor reinforces the conditioning process where the odor is associated with food.

During the bulk conditioning phase in the staging area, the target odor is associated with a food source by incorporating it into bulk feeders which are placed in the vicinity of the hives. Further, the bees are actively reoriented toward the bulk feeders by a variety of standard methods that include, but are not limited to: marking a syrup trail from the hive entrance to the feeder; inserting a small dish of syrup partially into the hive entrance, then gradually moving it to the main feeder as bees discover it; marking the feeder with bright colors that mimic surrounding nectar sources, then removing the visual attractant after the feeder is discovered. Hives stored in the staging area can be maintained in their conditioned state for more than 30 days with regular replenishment of fresh syrup and scent packets. To keep bees searching for scent labeled food sources, the bulk feeders are repositioned to random locations up to 100 meters from the hives every few days. After 24–48 hours, when bees are fully entrained on the bulk feeders, the hives are ready to be transported to the search area. The move is preferably performed at night, so as not to lose any of the entrained foraging worker force.

The hives are arrayed at the search site to focus flight over the area to be searched. The number of hives used and their placement is dictated by the terrain and area to be searched. Hives can be positioned singly or in clusters. Minimum distance from the edge of the search area should be approximately 50 meters to reduce unintentional overflight by bees orienting in the vicinity of the hives. Concurrent with deployment of hives to the search area, feeding stations using the feeding/conditioning means are set up within about 2 meters of the hive entrances. Feeding stations are stocked with concentrated sucrose syrup and linked to an automatic syrup replenishing system described below. The feeding system is specially designated to associate food reward with the odor signature of the target compound(s) and should be the same as was used in the bulk conditioning phase. The feeders are charged so that the first foragers emerging at daybreak will begin feeding on the odor marked feeders. In this way conditioning is not broken and the bees stay focused on the target odor. On the first day of foraging at the search site, bees are introduced to the feeding/conditioning means. As the population of bees using the feeding/conditioning means increases to a predetermined density (for example, about 50–100 bees on a bulk feeding plate, described below), conditioning to the target odor is judged to be present. Thereafter, a programmed feeding and starvation interval is initiated using an automated system. The automatic feeding cycle is turned on at day break and continues throughout the active foraging period each day. The system is timed to allow foraging bees to remove most of the syrup reward from the trays, then to allow an additional starvation period during which subsequent foragers will search the surrounding area for additional sources of the reward. At the end of the starvation period, the feeding trays are refilled and the feeding/starvation cycle is repeated. The reward and starvation intervals are programmed to flush bees away from the feeders and over the search area at regular intervals, but not so long as to break conditioning. With renewal of the syrup reservoirs, continuous conditioning on the target chemical odor can be maintained for several weeks. The exact intervals of starvation between feedings varies with the activity of the colonies and the environmental conditions in the search area. The interval can be between about 15 and 120 minutes, but is most often approximately 30 minutes where the intended target offers no reward to reinforce by fidelity.

Figure 2:
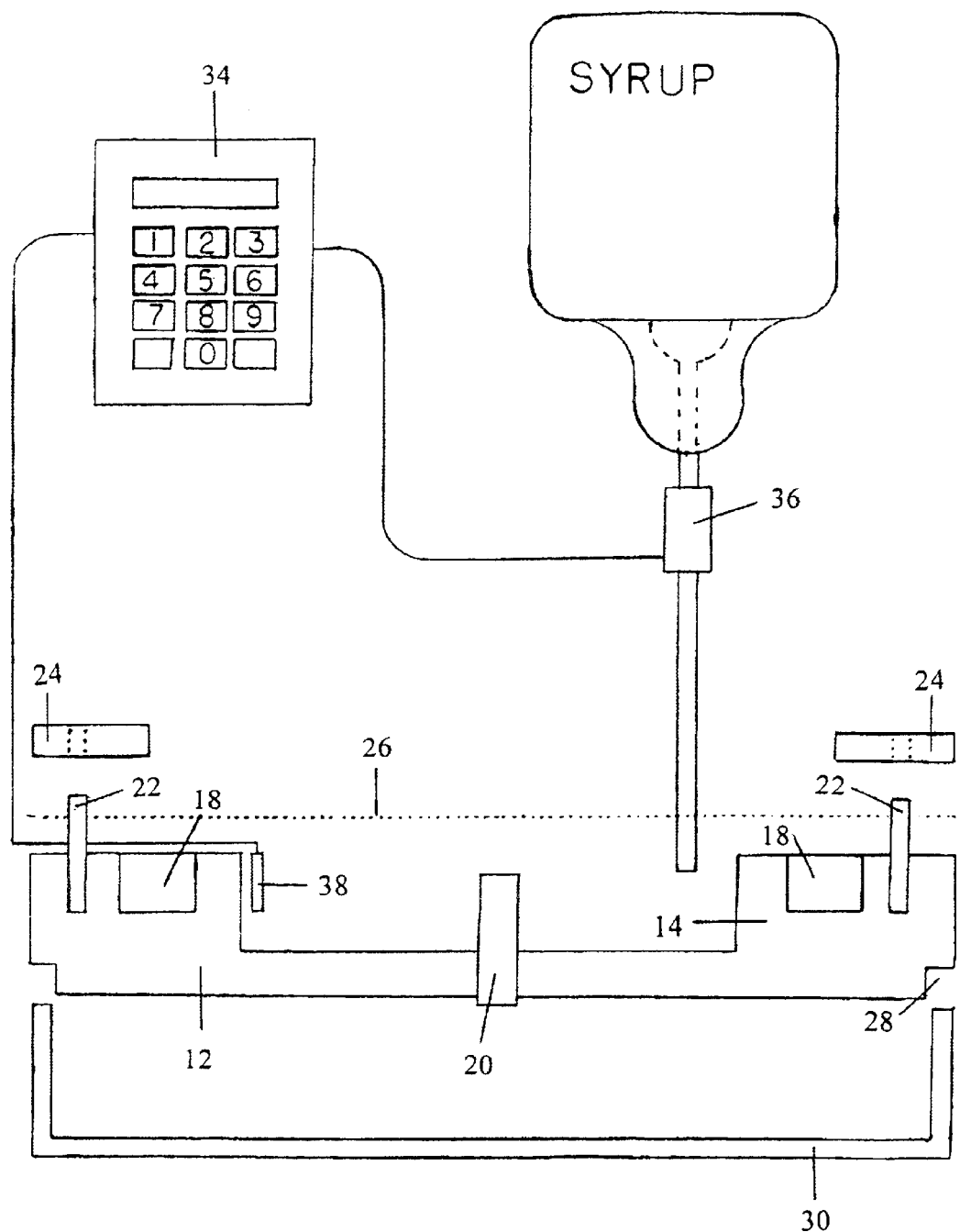
FIG. 2 is a side elevational view of the preferred embodiment of the feeding/conditioning means shown in FIG. 1.
Figure 3:
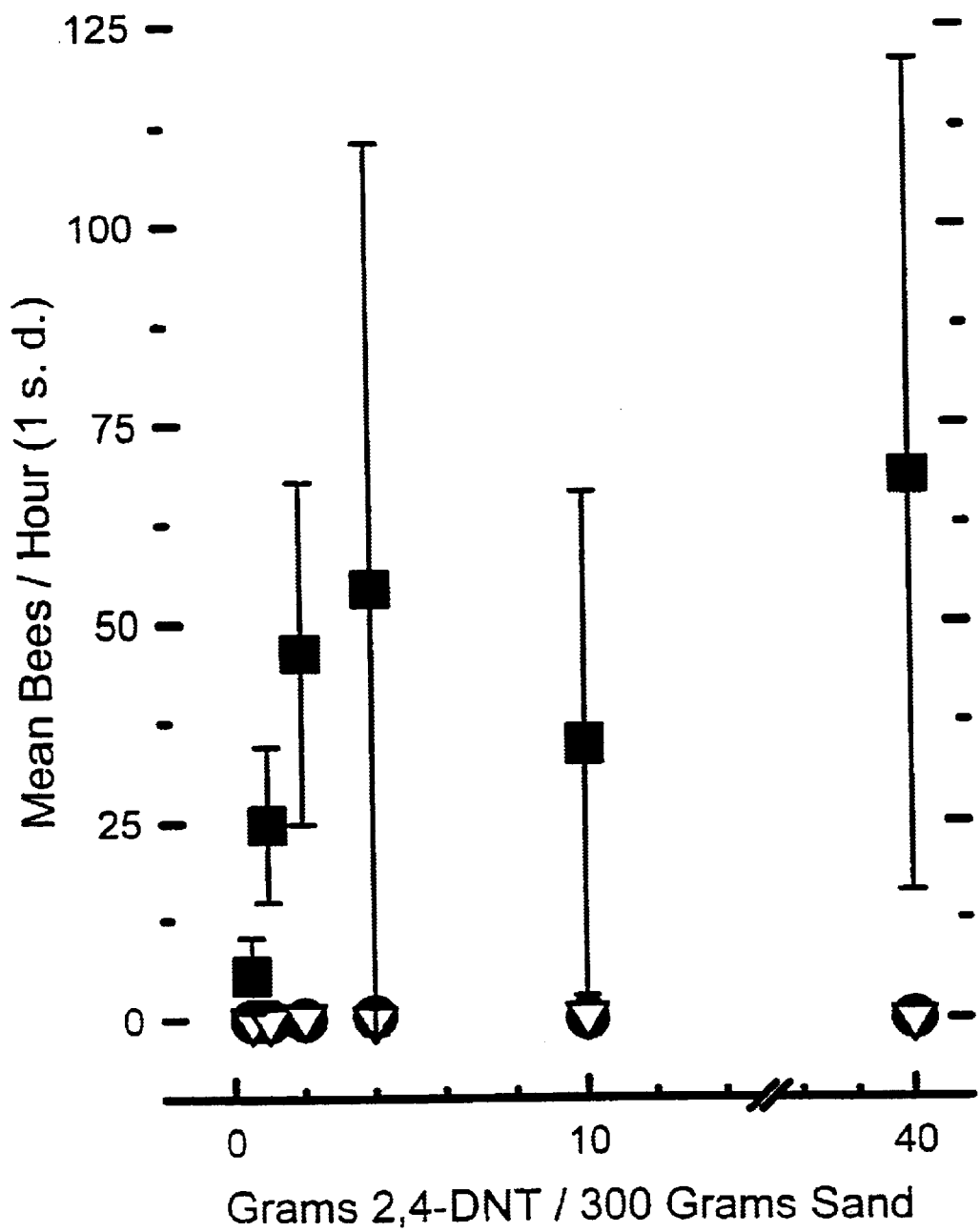
FIG. 3 shows the comparison of honey bee visits per hour over 2,4-DNT targets (□), control areas (○) and empty sites (▽) at varying DNT concentrations.
Figure 4:
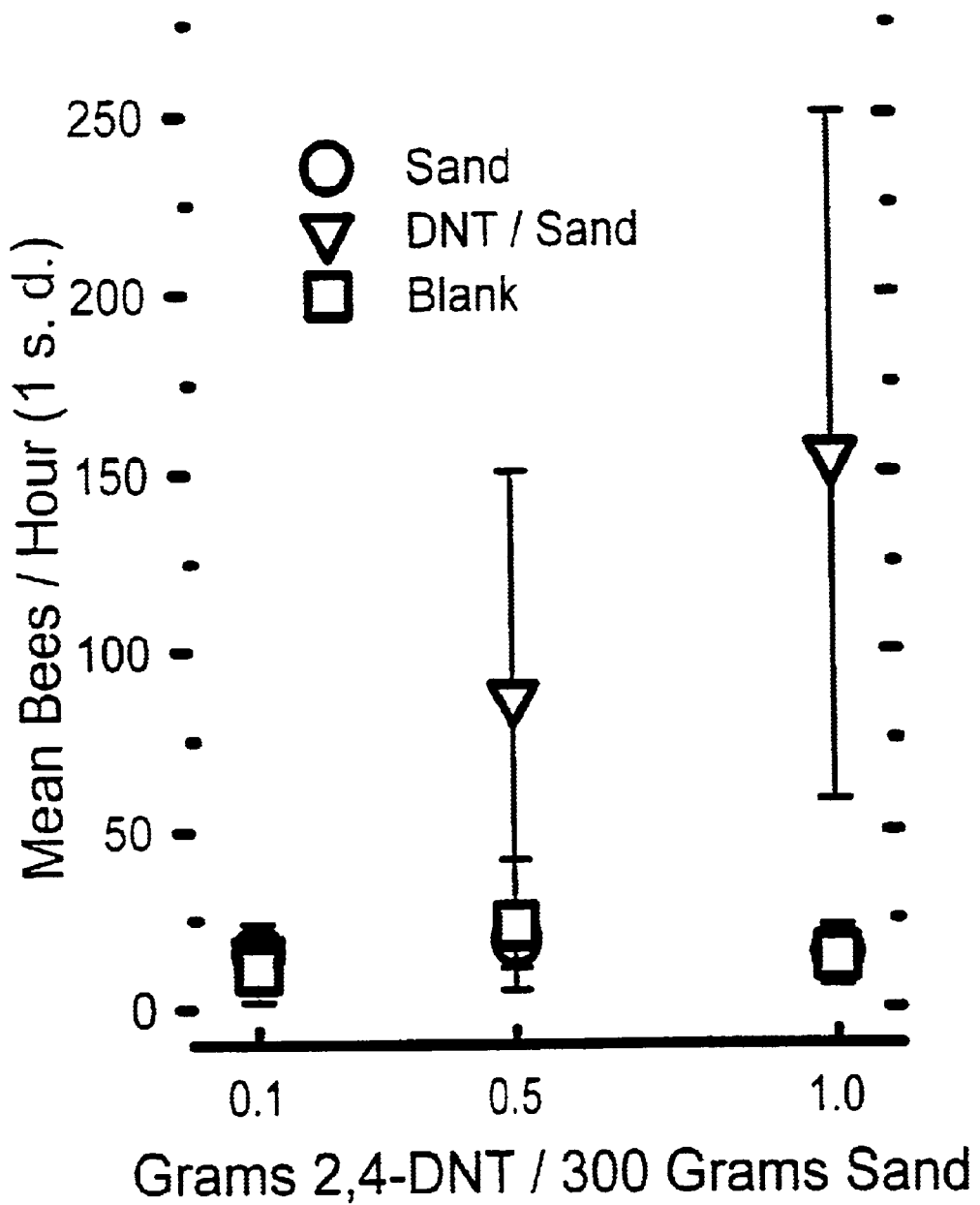
FIG. 4 shows the comparison of honey bee visits to 2,4-DNT targets (▽), control areas (○) and blank areas (□) in diminishing DNT concentrations.

Preferred embodiments of feeding/conditioning means are shown in FIGS. 1 and 2. FIGS. 1 and 2 show a feeding/conditioning means which is a feeding plate 10 manufactured of transparent acrylic. The diameter and shape of the dish can vary, but includes the same basic design regardless of the diameter and shape. For example, in a specific embodiment, the base 12 of the feeding plate is a solid cylinder 5 cm tall and between 20 and 30 cm diameter. The upper surface 14 of the cylinder is routed to produce a center well 16 about 1.5 cm deep. A concentric outer channel 18 about 1.5 cm wide and 1.5 com deep is routed between the well and the outer edge of the feeding plate. An overflow tube 20, 9 mm in diameter and 1.3 cm high is mounted in the center of the well, passing through the feeding plate. A transparent acrylic hold down ring 24 fits over the studs. A circle of standard aluminum window screening 26 fits between the top surface of the feeding plate and the hold-down ring to provide a surface for the bees to land and from which to feed on the syrup contained in the well. The ability to land and probe with the proboscis is an essential foraging behavior that reinforces the conditioning program.

The bottom 28 of the feeding plate is rabbetted to set into an overflow collector 30. The overflow collector 30 is constructed of transparent acrylic. It is cylindrical with diameter sized to receive the feeding plate. Its height is 4 cm. The depth can be increased to handle larger overflow, but should not exceed 10 cm. Together the assembled feeding plate and overflow collector do not exceed 10 cm height in order to condition bees to searching for the odor and reward close to the surface of the ground. When in use the feeding plates have chemical odorant added to the outer channel 18 to prevent contamination of the syrup in the feeder. The screen 26 and hold-down ring 24 are secured and the plate is connected to an automatic feeder.

Another preferred embodiment of the feeding/conditioning means used in the method of the subject invention allows larger numbers of bees to be conditioned and fed. The feeding/conditioning means is a trough filled with syrup covered by a screen insert upon which the bees can light and probe. Scent is associated with the trough by hanging scent packets along the side of the trough making certain the scent does not contaminate the food source. The trough is supported above the ground near the height at which the bees will search for the target.

Although programmed delivery of food reward is integral to the subject conditioning process, there is some latitude in the nature of the delivery system that will still accomplish conditioning. Any system that will regulate feeding and starvation cycles at the intervals described in the conditioning program above will successfully condition bees. The feeding controller delivery means preferably, is a programmable digital timer 34 and relay system that dispenses syrup to the feeding plates. Depending on the applications, the relays open and shut solenoids that release syrup via a gravity flow system or switch on and off pumps 36. The pumps can be either an in-line pump, or external peristaltic pumps. The choice of gravity flow versus pump, and the type of pump, depends on the application. Gravity flow provides the simplest system, but must be positioned close to the above feeding plates. Pumps provide positive force and can pull or push syrup to distant feeders.

In a preferred embodiment, the automated feeding controller delivery means consists of an automated timer/controller, such as an ALTRONIX. The timer system is programmed to turn four separate relays on or off at specific times and dates. These relays are connected to an overflow feedback unit 38 which in turn is connected to either a solenoid valve or a fluid pump. The overflow feedback unit monitors the level of fluid (food) in the feeder tray. If the level is too high, the feedback unit will override the timer/controller and will turn off the solenoid or fluid pump, preventing overflow of the feeder. Gravity provides liquid flow to the bulk feeding means. The valve operates as a vacuum control; when open vacuum inside the container is equalized and the liquid flows. Conversely, the container in the fluid pump version is a collapsible container.

Six independent trials were conducted in both Texas and Montana employing one hive searching for a simulated land mine within a 23 meter radius (0.17 hectare area). Twelve independent trials were conducted in Texas employing three hives searching for the same target within a 100 meter radius (3.14 hectare area). Land mines were simulated using variable vapor concentrations from 28 ppt to more than 500 ppt of 2,4-DNT (dinitrotoluene) under field conditions. Based on one hour trials and upper control counts for unambiguous detection calculated from observations of bees over bare soil and control sites, 100% detection (24/24) was observed of simulated mines at vapor concentrations above 80 ppt. At the threshold of detection below 30 ppt vapor concentration, a 33% detection rate (4/12) was observed for one hour detection trials. Successful conditioning of bees to locate 2,4-DNT targets is reflected in average bee counts over targets, blank areas and control sites illustrated in FIGS. 5 and 6. Statistical analysis confirmed that the 6 to 100 fold increases in bee visits over DNT targets is highly significant.

It is understood that the foregoing examples are merely illustrative of the present invention. Certain modifications of the articles and/or methods employed may be made and still achieve the objectives of the inventions. Such modifications are contemplated as within the scope of the claimed invention.

What is claimed is:

1. A method for conditioning honey bees to search for a target odor at a search area comprising the steps of:
   a) moving at least one honey bee hive containing bees to a staging area;
   b) applying the target odor to the at least one hive;
   c) placing at least one feeding and conditioning means comprising food and the target odor near the hive;
   d) reorienting the bees to the at least one feeding and conditioning means for a period of about 24 to about 48 hours;
   e) moving the at least one hive to the search area;
   f) positioning at least one feeding and conditioning means proximate the at least one hive;
   g) feeding the bees at the at least one feeding and conditioning means for about 24 hours; and
   h) alternating periods of feeding and periods of starvation to encourage the bees to forage and identify the target odor.

2. The method of claim 1, wherein said staging area is at least two miles from said search area.

3. The method of claim 1, wherein said bees are reoriented to said at least one feeding and conditioning means by methods selected from the group consisting of: making a food trail from an entrance of said at least one hive to said at least one feeding and conditioning means; inserting a dish of food partially into the entrance of said at least one hive and moving it gradually toward said at least one feeding and conditioning means and creating a marking on said at least one feeding and conditioning means in bright colors to mimic surrounding nectar sources and removing the marking after said bees discover said at least one feeding and conditioning means.

4. The method of claim 1, wherein said at least one hive is moved to said search area at night.

5. The method of claim 1, wherein said feeding and conditioning means are positioned about two meters from said at least one hive in said search area.

6. The method of claim 1, wherein periods of starvation between periods of feeding are between about 15 minutes and about 120 minutes.

7. The method of claim 6, wherein said periods of starvation are about 30 minutes.

8. The method of claim 1, wherein said feeding and conditioning means comprise:
   a base, wherein an upper surface of the base comprises a well to hold said food and a channel separate from the well to hold said target odor;
   a screen covering the upper surface of the base; and
   a ring disposed above the screen and removably attached to the base;
   wherein the bees land on the screen and probe the food in the well.

9. The method of claim 8, wherein said base is a solid cylinder.

10. The method of claim 9, wherein said well is circular and proximate the center of said upper surface of said cylinder and said channel encircles said well.

11. The method of claims 10, wherein said base which is a solid cylinder is about 5 centimeters high and about 20 centimeters to about 30 centimeters in diameter, and said well is about 1.5 centimeters deep and said channel is about 1.5 centimeters wide and about 1.5 centimeters deep.

12. The method of claim 8, wherein said feeding and conditioning means further comprises an overflow tube protruding through said base into said well.

13. The method of claim 12, wherein said feeding and conditioning means further comprises an overflow collector.

14. The method of claim 13, wherein said feeding and conditioning means and said overflow collector together are not greater than about 10 centimeters high.

15. The method of claim 1, wherein said alternating periods of feeding and period of starvation are controlled by an automated feeding controller delivery means comprising:
- a programmable timer capable of controlling at least one relay;
- an overflow feedback unit to monitor the level of said food in said well; and
- a pump.

16. Feeding and conditioning means for feeding and conditioning honey bees to a target odor comprising:
- a base, wherein an upper surface of the base comprises a well to hold food and a channel separate from the well to hold said target odor;
- a screen covering the upper surface of the base; and
- a ring disposed above the screen and removably attached to the base;

wherein the bees land on the screen and probe the food in the well.

17. The feeding and conditioning means of claim 16, wherein said base is a solid cylinder.

18. The feeding and conditioning means of claim 17, wherein said well is circular and proximate the center of said upper surface of said cylinder and said channel encircles said well.

19. The feeding and conditioning means of claim 18, wherein said base which is a solid cylinder is about 5 centimeters high and about 20 centimeters to about 30 centimeters in diameter, and said well is about 1.5 centimeters deep and said channel is about 1.5 centimeters wide and about 1.5 centimeters deep.

20. The feeding and conditioning means of claim 16, wherein said feeding and conditioning means further comprises an overflow tube protruding through said base into said well.

21. The feeding and conditioning means of claim 20, wherein said feeding and conditioning means further comprises an overflow collector.

22. The feeding and conditioning means of claim 21, wherein said feeding and conditioning means and said overflow collector together are not greater than about 10 centimeters high.

23. The feeding and conditioning means of claim 16, further comprising an automated feeding controller delivery means comprising:
- a programmable timer capable of controlling at least one relay;
- an overflow feedback unit to monitor the level of said food in said well; and
- a pump.

* * * * *